US010034971B2

(12) United States Patent
Abu-Sultaneh et al.

(10) Patent No.: US 10,034,971 B2
(45) Date of Patent: Jul. 31, 2018

(54) TUBE SECURING DEVICE

(71) Applicant: Indiana University Research and Technology Corporation, Indianapolis, IN (US)

(72) Inventors: Samer Abu-Sultaneh, Carmel, IN (US); Terri Bogue, Carmel, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 332 days.

(21) Appl. No.: 14/860,030

(22) Filed: Sep. 21, 2015

(65) Prior Publication Data
US 2016/0082163 A1 Mar. 24, 2016

Related U.S. Application Data

(60) Provisional application No. 62/053,328, filed on Sep. 22, 2014.

(51) Int. Cl.
*A61M 25/02* (2006.01)
*A61M 39/00* (2006.01)
*A61M 1/00* (2006.01)

(52) U.S. Cl.
CPC ............ *A61M 1/008* (2013.01); *A61M 25/02* (2013.01); *A61M 2025/024* (2013.01); *A61M 2025/028* (2013.01)

(58) Field of Classification Search
CPC .......... A61M 2025/0273; A61M 1/008; A61M 25/02; A61M 2025/028; A61M 2025/024; A61M 2025/0246; A61M 2005/1586; A61M 2025/0253; A61M 2025/026; A61M 2025/0266; Y10S 128/26; Y10S 128/06
See application file for complete search history.

(56) References Cited

U.S. PATENT DOCUMENTS

| | | | | |
|---|---|---|---|---|
| 4,881,705 A * | 11/1989 | Kraus | ........................ | F16L 3/08 248/68.1 |
| 5,184,794 A * | 2/1993 | Saito | ......................... | F16L 3/13 248/316.5 |
| 5,693,032 A * | 12/1997 | Bierman | ................ | A61M 25/02 604/174 |
| 5,996,945 A * | 12/1999 | Coles | ..................... | F16L 3/2235 24/16 R |
| 6,213,979 B1 * | 4/2001 | Bierman | ................ | A61M 25/02 128/DIG. 26 |
| 6,382,568 B1 * | 5/2002 | Snell | ......................... | F16L 3/22 128/DIG. 26 |
| 6,572,588 B1 * | 6/2003 | Bierman | ................ | A61M 25/02 128/DIG. 26 |
| 2006/0015072 A1 * | 1/2006 | Raulerson | .............. | A61M 25/02 604/180 |
| 2007/0142784 A1 * | 6/2007 | Dikeman | ............... | A61M 25/02 604/174 |

(Continued)

*Primary Examiner* — Adam Marcetich
(74) *Attorney, Agent, or Firm* — Faegre Baker Daniels LLP

(57) ABSTRACT

A tube securing device is provided comprising a base, a tube mount including a tube receptacle configured to receive a tube in communication with a cavity of a patient, a retainer, and at least one fastener mounted to one of the base and the retainer and configured to cooperate with the other of the base and the retainer to retain the tube mount between the base and the retainer.

18 Claims, 3 Drawing Sheets

(56) References Cited

U.S. PATENT DOCUMENTS

| | | | |
|---|---|---|---|
| 2008/0125718 A1* | 5/2008 | Tsuchiya | A61M 25/02 604/174 |
| 2009/0143742 A1* | 6/2009 | Bracken | A61M 25/02 604/180 |
| 2011/0118670 A1* | 5/2011 | Kay | A61M 25/02 604/177 |
| 2012/0217353 A1* | 8/2012 | Hennon | F16L 3/1091 248/67.5 |
| 2013/0079721 A1* | 3/2013 | Mizoguchi | A61M 25/02 604/174 |
| 2014/0163515 A1* | 6/2014 | Hyman | A61M 25/02 604/500 |
| 2015/0141962 A1* | 5/2015 | Collins | A61M 25/02 604/513 |
| 2016/0334044 A1* | 11/2016 | Koenig | F16L 55/035 |

* cited by examiner

TUBE SECURING DEVICE

RELATED APPLICATIONS

The present application is based on and claims priority to U.S. Provisional Application Ser. No. 62/053,328, filed Sep. 22, 2014, entitled "CHEST TUBE SECURING DEVICE," the entire disclosure of which being hereby incorporated herein by reference.

FIELD OF THE DISCLOSURE

The present disclosure is related to a device for securing tubes, such as chest tubes to a patient. The present disclosure is related more specifically to a tube securing device that is attached to a patient's body with an adhesive band.

BACKGROUND

Chest tubes are flexible plastic tubes that are used to drain fluids or gases that have accumulated in the pleural space. Chest tube placement, known as tube thoracotomy, involves the following steps: administering a local anesthetic to the patient's chest, creating an incision between the patient's ribs, feeding a chest tube into the patient's pleural space, securing the chest tube, and allowing the fluid and/or gas to drain, with or without the assistance of suction. At present, the act of securing the chest tube is often accomplished by suturing the tube directly to the patient. This technique has several disadvantages. First, sutured chest tubes, especially smaller sized tubes, often become dislodged from patients. When a sutured tube dislodges, the patient can experience bleeding, pain, and even pneumothorax. Second, suturing takes a substantial amount of time. Suturing is disadvantageous in emergency situations, when time is of the essence. Third, suturing may limit the patient's movement because the chest tube is prone to dislodgment.

Accordingly, there exists the need for a device that can secure a chest tube to a patient without requiring health professionals to suture the tube in place.

SUMMARY

In one embodiment, the present disclosure provides a tube securing device comprising a base, a tube mount including a tube receptacle configured to receive a tube in communication with a cavity of a patient, a retainer, and at least one fastener mounted to one of the base and the retainer and configured to cooperate with the other of the base and the retainer to retain the tube mount between the base and the retainer. In one aspect of this embodiment, the device further comprises an adhesive strip attached to a lower wall of the base, the adhesive strip including a lower surface having an adhesive to attach the device to the patient. In another aspect, the base includes a groove sized to receive the tube receptacle of the tube mount. In a variant of this aspect, the groove includes a curved inner surface. In another aspect the tube receptacle has a cylindrical wall and defines an opening for receiving the tube. In a variant of this aspect, the opening of the tube receptacle is operable to receive tubes having outer diameters within the range of 6 Fr to 40 Fr. In still another aspect, the fastener is connected to an upper wall of the base. In a variant, the retainer includes a receptacle for receiving the fastener to thereby attach the retainer to the base and retain the tube mount between the base and the retainer. In a further variant, the tube mount includes a body having an opening that permits the fastener to extend through the body from the upper wall of the base to the receptacle of the retainer. In yet another aspect of this embodiment, the cylinder comprises rubber. In another aspect, the base and the retainer comprise polyvinyl chloride.

In another embodiment, the present disclosure provides a method of securing a tube to a patient comprising inserting the tube through an opening in a tube receptacle of a tube mount, placing the tube receptacle into a groove of a base, attaching a retainer to the base using at least one fastener, thereby retaining the tube mount between the base and the retainer, and adhering the base to the patient. In one aspect of this embodiment, adhering includes attaching an adhesive strip to a lower wall of the base. In another aspect, inserting includes placing one end of the tube through a longitudinal opening extending through the tube receptacle. In yet another aspect, inserting includes opening a side wall of the tube receptacle and passing a portion of the tube through the side wall opening into the opening of the tube receptacle. In yet another aspect of this embodiment, attaching includes passing a pair of fasteners connected to a top wall of the base through openings in a body of the tube mount and into a pair of receptacles formed in the retainer. In another aspect, the base and the retainer are formed of PVC and the tube receptacle is formed of rubber. In yet another aspect, the tube receptacle is cylindrical in cross-section and the groove is sized to receive the tube receptacle. In a further aspect, the tube receptacle is sized to receive chest tubes within one of the ranges of 16 Fr to 22 Fr and 28 Fr to 36 Fr.

In yet another embodiment of the present disclosure, a chest tube securing device is provided comprising a base having a top wall, a bottom wall, a front wall, a rear wall, a plurality of fasteners extending from the top wall, and a groove formed into the top wall and extending between the front wall and the rear wall, a tube mount including a body having a plurality of openings and a tube receptacle configured to receive a tube in communication with a chest cavity of a patient, the tube receptacle being sized to be received by the groove in the top wall of the base, a retainer having a top wall, a bottom wall, and a plurality of receptacles extending into the retainer from the bottom wall, the plurality of receptacles being aligned with the plurality of openings in the tube mount body and the plurality of fasteners to receive the fasteners and retain the tube mount between the base and the retainer, and an adhesive strip attached to the bottom wall of the base and having a lower surface with an adhesive to attach the chest tube securing device to the patient.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION OF THE DRAWINGS

The embodiments disclosed herein are not intended to be exhaustive or to limit the disclosure to the precise forms disclosed in the following detailed description. Rather, the embodiments were chosen and described so that others skilled in the art may utilize their teachings.

Figure 1:
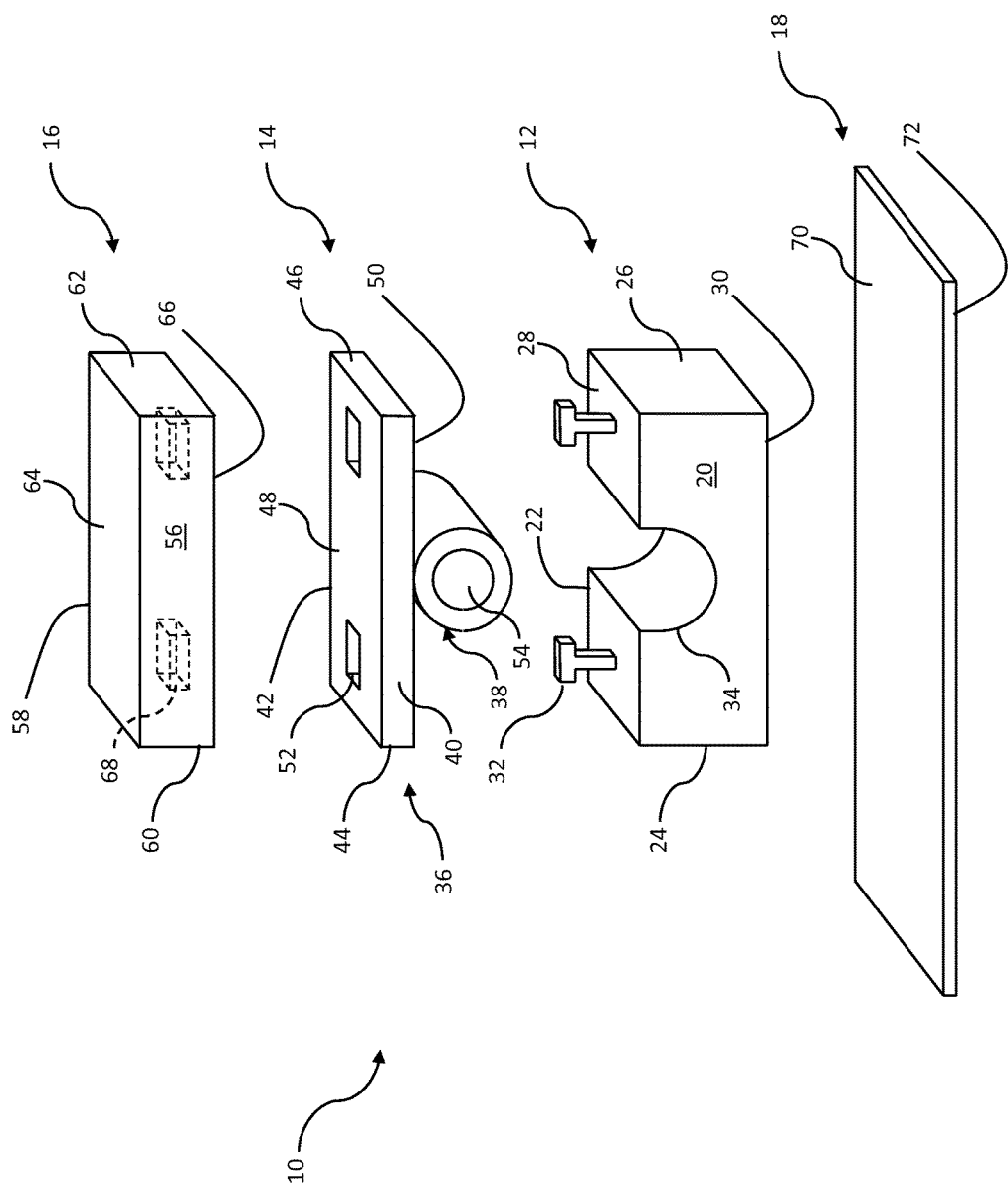
FIG. 1 is a perspective view illustrating components of one embodiment of a tube securing device according to the principles of the present disclosure.

A first representative embodiment of the present disclosure is shown in FIG. 1. As shown, an exemplary tube securing device 10 generally includes a base 12, a tube mount 14, a retainer 16 and an adhesive strip 18. While portions of this disclosure describe the tube securing device 10 in the context of securing chest tubes, it should be understood that device 10 may have many other tube securing applications, all of which are intended to be within the scope of the present disclosure. In one embodiment, base 12 includes a front wall 20, a rear wall 22, side walls 24, 26, a top wall 28, a bottom wall 30 and fasteners 32. Base 12 further includes a recess or groove 34 that extends from front wall 20 to rear wall 22 and is opened to top wall 28. Groove 34 is sized to approximate the diameter of a component of tube mount 14 as is further described below.

Fasteners 32 are depicted as being male fasteners of a particular shape, and later described as cooperating with female receptacles of retainer 16 for securing tube mount 14 within device 10. As will be apparent to those skilled in the art, however, fasteners 32 may have any of a variety of suitable shapes, be located at various locations of base 12, or be located on retainer 16. In other words, fasteners 32 need not be T-shaped, but may be formed to resemble a hook, a prong, a stud, an L-shape, etc. Fasteners 32 need not be mounted to top wall 28 of base 12, but may be connected to one or more of side walls 24, 26, front wall 20, rear wall 22, etc. Moreover, fasteners 32 may be connected to retainer 16, and base 12 may include female receptacles to cooperate with fasteners 32 to secure tube mount 14 within device 10. Additionally, fasteners 32 may be snaps, Velcro®, toggle latches, catch bolts, toggle clamps, removable elastic bands or straps or any other structure that provides cooperation between base 12 and retainer 16 to secure tube mount 14 between base 12 and retainer 16.

In one application, tube securing device 10 is operable to secure a chest tube to a patient's person without the use of sutures. As such, device 10 may lower the risk of chest tube dislodgement, especially when using small chest tubes, enhance patient mobility, and lower the amount of time needed to secure chest tubes.

In the depicted embodiment, tube mount 14 generally includes a body 36 and a tube receptacle 38. Body 36 includes a front wall 40, a rear wall 42, side walls 44, 46, a top wall 48, and a bottom wall 50. In certain embodiments, body 36 further includes openings 52 for receiving fasteners 32 in the manner described below. Body 36 is depicted as being generally plate shaped and having lateral dimensions that generally approximate the lateral dimensions of base 12. It should be understood, however, that body 36 may have any of a variety of different shapes and dimensions, and is intended to provide a structure to attach to tube receptacle 38 and permit tube receptacle 38 to be secured to device 10.

Tube receptacle 38 is shown mounted or attached to bottom wall 50 of body 36. It should be understood, however, that tube 38 and body 36 may be formed as one piece or more than two pieces. Tube receptacle 38 is depicted as being cylindrical in shape, and having a central opening 54 with a diameter sufficient to receive a tube (e.g., a chest tube). Tube receptacle 38 may, however, be non-cylindrical in shape. Additionally, tube receptacle 38 may have a longitudinal slit or gap (not shown) that permits a side of receptacle 38 to be opened for receiving a tube into opening 54 laterally, rather than through an end of receptacle 38. Body 36 and tube receptacle 38 may be formed of resilient materials such as rubber or other material. Rubber may be a particularly advantageous material because it is widely available, flexible, and forms a very tight fit with PVC (a material suitable for base 12 and retainer 16). As used in tube receptacle 38, rubber may serve the dual purpose of securing a tube and preventing receptacle 38 from moving within groove 34 of base 12.

Retainer 16 includes a front wall 56, a rear wall 58, side walls 60, 62, a top wall 64, a bottom wall 66 and receptacles 68. As explained above, retainer 16 may include fasteners 32 instead of receptacles 68. Retainer 16 is depicted as being generally plate shaped and having lateral dimensions that generally approximate the lateral dimensions of body 36 of tube mount 14 and base 12. It should be understood, however, that retainer 16 may have any of a variety of different shapes and dimensions, and is intended to provide a structure that cooperates with base 12 to secure tube mount 14 to device 10.

Finally, adhesive strip 18 generally includes an upper surface 70 and a lower surface 72. Upper surface 70 and/or lower surface 72 may include a pressure sensitive adhesive (PSA), which is a viscoelastic adhesive material that requires a light amount of pressure, such as pressing down, in order to adhere to a surface. PSAs are a common class of medical adhesives because they typically adhere to human skin without greatly damaging the skin when removed. Examples of PSAs include, but are not limited to, silicone adhesives, acrylic adhesives, polyolefins, polyurethane, synthetic rubber, and natural rubber. In a more particular embodiment, adhesive strip 18 is coated on upper surface 70 and lower surface 72 with a PSA. In another embodiment, only lower surface 72 (i.e., the surface that interacts with the patient's skin) is coated with a PSA. In other embodiments, adhesive strip 18 is coated with a non-PSA adhesive material, such as an epoxy or a cyanoacrylate adhesive. In some embodiments, adhesive strip 18 is a tape made of paper, cloth, or a synthetic solid material, such as silicone, that is coated with a PSA. Generally, upper surface 70 of adhesive strip 18 is attached to lower wall 30 of base 12 ad lower surface 70 of adhesive strip 18 is attached to the patient's skin.

Figure 2:
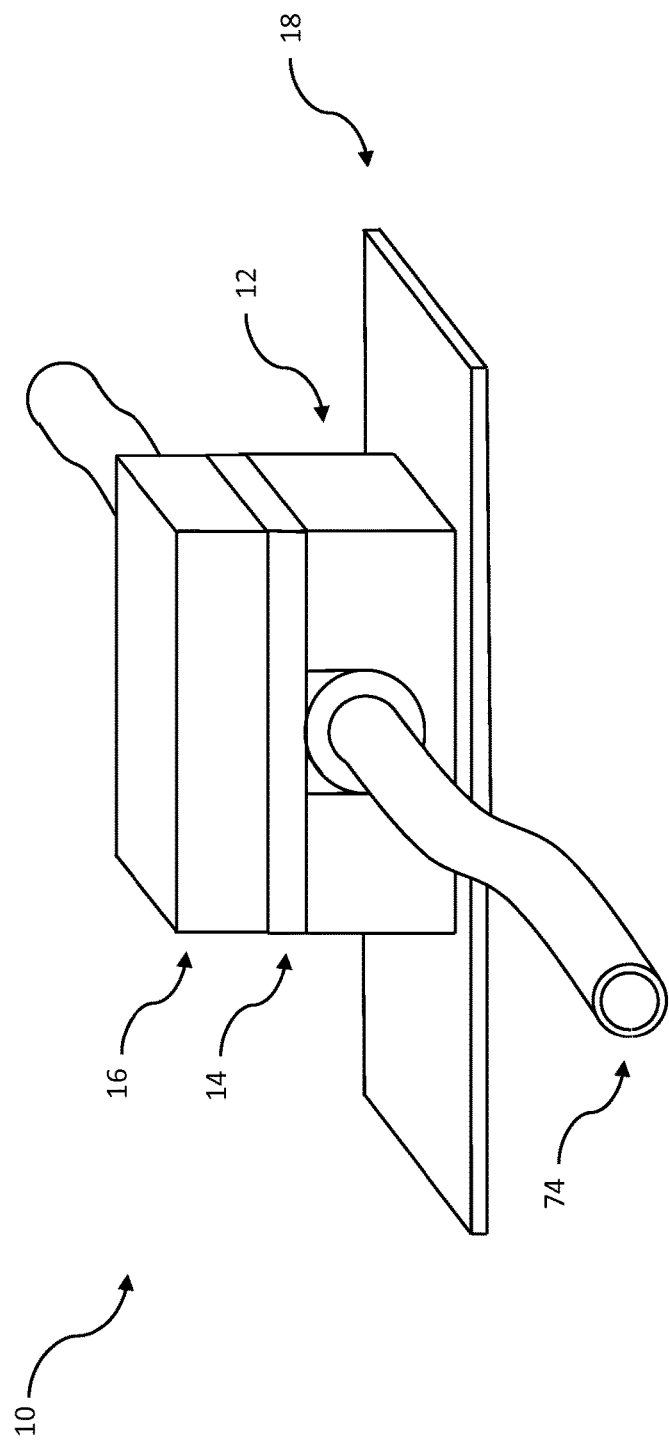
FIG. 2 is a perspective view of the device of FIG. 1 in a fully assembled state.

A fully assembled tube securing device 10 securing a tube 74 (such as a chest tube) is depicted in FIG. 2.

In one embodiment of the present disclosure, tube securing device 10 is used in the following manner. Tube 74 (such as a chest tube) is first passed through opening 54 of tube receptacle 38. The interior diameter of opening 54 may be sized to accommodate a wide range of chest tube sizes. Smaller size chest tubes, within the range of 16 Fr to 22 Fr, are typically used to treat pneumothorax. Small sized chest tubes are suitable for pneumothorax because pleural gas can easily pass through smaller tubes. Additionally, small bore chest tubes are typically easier to insert and cause less pain to the patient. In circumstances where the patient is suffering from a pleural effusion, for example hemothorax or pyothorax, a larger sized chest tube must typically be used to remove the fluid. A typical chest tube size employed when treating a pleural effusion ranges from 28 Fr to 36 Fr. These size ranges are illustrative and can shift depending on the body size of the patient. For example, a pediatric patient will often require a much smaller chest tube size than an adult patient. It should be understood that tube securing devices 10 having different dimensions to accommodate different size chest tubes may be manufactured and made available to health care providers for selection during surgeries.

After tube 74 is positioned within opening 54, tube mount 14 is placed onto base 12 such that tube receptacle 38 is situated within groove 34. In certain embodiments, such placement of tube mount 14 causes openings 52 of tube mount body 36 to pass over fasteners 32 of base 12 such that fasteners 32 protrude through openings 52 for connection to receptacles 68 of retainer 16. In one exemplary embodiment, base 12 is a rectangular body of polyvinyl chloride (PVC). Retainer 16 may also be formed of PVC. In one exemplary embodiment, rubber padding (not shown) is coupled to the curved inner surface of groove 34.

Next, retainer 16 is placed onto tube mount body 36 such that receptacles 68 of retainer 16 engage fasteners 32 of base 12 to retain tube mount 14 in place. In certain embodiments, retainer 16 may apply a compressive force to body 36 when attached to fasteners 32. Finally, adhesive strip 18 is attached to lower wall 30 of base 12. It should be understood, however, that adhesive strip 18 may be attached to base 12 before, during or after the above-described assembly of the other components of device 10.

Figure 3:
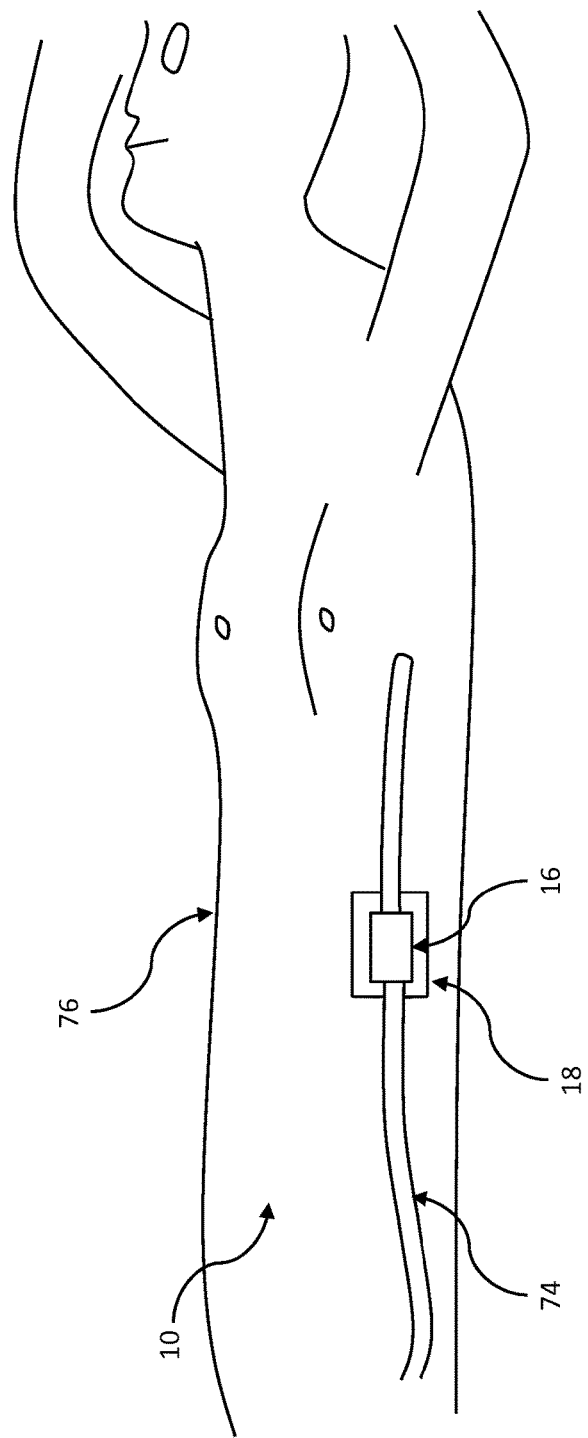
FIG. 3 illustrates one embodiment of a fully assembled tube securing device attached to a supine patient.

FIG. 3 illustrates a completed tube securing device 10 on the chest of supine patient 76 functioning to secure a chest tube 74. In this illustration, chest tube 74 is secured by tube securing device 10, and chest tube 74 has been positioned into supine patient 22's pleural space. Typically, chest tube 74 will be placed into the patient's pleural space before tube securing device 10 is coupled to supine patient 22.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A tube securing device comprising:
    a base;
    a tube mount including a tube receptacle configured to removably receive a tube in communication with a cavity of a patient;
    a retainer; and
    at least one fastener mounted to one of the base and the retainer and configured to pass through the tube mount to cooperate with the other of the base and the retainer to retain the tube mount between the base and the retainer; and
    an adhesive strip attached to a lower wall of the base, the adhesive strip including a lower surface having an adhesive configured to attach the device to the patient;
    wherein the base includes a groove sized to receive the tube receptacle of the tube mount.

2. The device of claim 1 wherein the groove includes a curved inner surface.

3. The device of claim 1 wherein the tube receptacle has a cylindrical wall and defines an opening for receiving the tube.

4. The device of claim 3 wherein the opening of the tube receptacle is operable to receive tubes having outer diameters within the range of 6 Fr to 40 Fr.

5. The device of claim 1 wherein the fastener is connected to an upper wall of the base.

6. The device of claim 5 wherein the retainer includes a receptacle for receiving the fastener to thereby attach the retainer to the base and retain the tube mount between the base and the retainer.

7. The device of claim 6 wherein the tube mount includes a body having an opening that permits the fastener to extend through the body from the upper wall of the base to the receptacle of the retainer.

8. The device of claim 1 wherein the tube receptacle comprises rubber.

9. The device of claim 1 wherein the base and the retainer comprise polyvinyl chloride.

10. A method of securing a tube to a patient comprising:
    removably inserting the tube through an opening in a tube receptacle of a tube mount;
    placing the tube receptacle into a groove of a base;
    attaching a retainer to the base using at least one fastener by passing the at least one fastener through the tube mount, thereby retaining the tube mount between the base and the retainer; and
    adhering the base to the patient.

11. The method of claim 10 wherein adhering includes attaching an adhesive strip to a lower wall of the base.

12. The method of claim 10 wherein inserting includes placing one end of the tube through a longitudinal opening extending through the tube receptacle.

13. The method of claim 10 wherein inserting includes opening a side wall of the tube receptacle and passing a portion of the tube through the side wall opening into the opening of the tube receptacle.

14. The method of claim 10 wherein attaching includes passing a pair of fasteners connected to a top wall of the base through openings in a body of the tube mount and into a pair of receptacles formed in the retainer.

15. The method of claim 10 wherein the base and the retainer are formed of PVC and the tube receptacle is formed of rubber.

16. The method of claim 10 wherein the tube receptacle is cylindrical in cross-section and the groove is sized to receive the tube receptacle.

17. The method of claim 10 wherein the tube receptacle is sized to receive chest tubes within one of the ranges of 16 Fr to 22 Fr and 28 Fr to 36 Fr.

18. A chest tube securing device comprising:
    a base having a top wall, a bottom wall, a front wall, a rear wall, a plurality of fasteners extending from the top wall, and a groove formed into the top wall and extending between the front wall and the rear wall;
    a tube mount including a body having a plurality of openings and a tube receptacle configured to removably receive a tube in communication with a chest cavity of a patient, the tube receptacle being sized to be received by the groove in the top wall of the base;
    a retainer having a top wall, a bottom wall, and a plurality of receptacles extending into the retainer from the bottom wall, the plurality of receptacles being aligned with the plurality of openings in the tube mount body and the plurality of fasteners to receive the fasteners and retain the tube mount between the base and the retainer; and
    an adhesive strip attached to the bottom wall of the base and having a lower surface with an adhesive to attach the chest tube securing device to the patient.

* * * * *